United States Patent [19]

Reedy

[11] Patent Number: 4,594,226
[45] Date of Patent: Jun. 10, 1986

[54] GAS CHROMATOGRAPHY/MATRIX-ISOLATION APPARATUS

[76] Inventor: Gerald T. Reedy, 411 Francis St., Bourbonnais, Ill. 60914

[21] Appl. No.: 583,042

[22] Filed: Feb. 23, 1984

[51] Int. Cl.$^4$ .................. G01J 1/00; G01N 21/01; G01N 30/02
[52] U.S. Cl. .................. 422/89; 250/338; 250/341; 250/304; 250/352
[58] Field of Search .................. 356/244, 426, 72; 250/352, 353, 338, 347, 341, 304, 348, 349, 342, 343; 422/83, 89

[56] References Cited

U.S. PATENT DOCUMENTS

| | | | |
|---|---|---|---|
| 4,047,498 | 9/1977 | Wood | 118/263 |
| 4,158,772 | 6/1979 | Reedy | 250/338 |
| 4,197,457 | 4/1980 | Cheo | 250/341 |
| 4,221,482 | 9/1980 | Macourt | 356/36 |
| 4,317,995 | 3/1982 | Bradshaw et al. | 250/286 |
| 4,330,318 | 5/1982 | Van Cauter et al. | 427/160 |
| 4,473,295 | 9/1984 | Doyle | 356/244 |

OTHER PUBLICATIONS

Letter to the Editor, Infrared Physics, 1975, vol. 15, pp. 339-340.
Infrared Analysis of Multicomponent Gas Mixtures, Rochkind, Analy. Chem., vol. 39, No. 6, 1967, pp. 567-574.

*Primary Examiner*—Michael S. Marcus
*Attorney, Agent, or Firm*—Emrich & Dithmar

[57] ABSTRACT

A gas-sample collection device provides matrix isolation of individual gas bands from a gas chromatographic separation and for the spectroscopic analysis of the individual sample bands. The device includes a vacuum chamber containing a rotatably supported, specular carousel having at least one reflecting surface for holding a sample deposited thereon. A gas inlet is provided for depositing a mixture of sample and matrix material on the reflecting surface which is maintained at a sufficiently low temperature to cause solidification. A first parabolic mirror directs an incident beam of electromagnetic radiation, such as in the infrared (IR) spectrum, from a source onto the sample/matrix mixture while a second parabolic mirror directs a second beam of electromagnetic radiation reflected by the specular surface to an IR spectrometer for determining the absorption spectra of the sample material deposited on the reflecting surface. The pair of off-axis parabolic mirrors having a common focal point are positioned outside of the vacuum chamber and may be displaced in combination for improved beam positioning and alignment. The carousel is provided with an aperture for each reflecting surface to facilitate accurate positioning of the incident beam relative to the gas-samples under analysis. Improved gas-sample deposition is insured by the use of a long focal length stereomicroscope positioned outside of the vacuum chamber for monitoring sample formation through a window, while the sample collector is positioned outside of the zone bounded by the incident and reflected electromagnetic beams for improved sample access and monitoring.

17 Claims, 10 Drawing Figures

INCIDENT
IR BEAM

GAS CHROMATOGRAPHY/MATRIX-ISOLATION APPARATUS

The U.S. Government has rights in this invention under Contract No. W-31-109-ENG38 between the U.S. Department of Energy and Argonne National Laboratory.

BACKGROUND OF THE INVENTION

This invention relates generally to the analysis of the composition of materials by means of spectroscopy and is particularly directed to a gas chromatographic/matrix-isolation device for the spectroscopic analysis of gas samples.

Gas chromatographic separations have been useful fundamental tools of chemical research and analysis for some time. Their usefulness is greatly enhanced when the separated components can be conveniently and promptly analyzed. The matrix-isolation technique for presenting samples for spectroscopic examination is also of considerable value in obtaining precise analysis of samples including specific structural information about molecular construction through high-resolution infrared analyses. The technique of matrix-isolation spectroscopy involves the simultaneous condensation of a gaseous sample in an excess of inert gas to form a solid matrix in which sample molecules are isolated from one another. The technique is powerful with respect to both the variety of species that can be studied and the quality of the spectra that can be obtained. Typically, a particular and distinct sample material is entrapped within a frozen matrix of an inert substance such as argon or krypton gas. These systems are typically maintained at very low temperatures, such as 10°-20° K. This technique permits the retention of the sample in a neutral and noncontaminating matrix material over an extended period of time. As a result, high resolution infrared and other spectroscopic types of analyses are available with this approach.

Although the cryogenic matrix isolation technique has been widely practiced in the theoretical study of molecules, it has not been widely used in analytical chemistry laboratories as a routine method for the spectroscopic identification of unknown compounds. This is primarily because this technique in the past has been slow and cumbersome and generally permitted only one or two compounds to be analyzed per run. This has, of course, been unfortunate because when used in combination with gas chromatography, which is a highly efficient and widely practiced method of separating complex mixtures of compounds, the matrix isolation technique is a powerful analytic tool.

To successfully combine these two methods and obtain matrix-isolation infrared spectra of the components eluted from a gas chromatograph, provision must first be made for collecting several components in rapid sequence. Secondly, for a given rate of elution of sample from the chromatograph, the rate of flow and condensation of the matrix-forming gas must be appropriate to maintain proper dilution of the sample in the matrix. Controlling these conditions for optimum spectral analysis has proven difficult and limited the extent of use and acceptance of the matrix-isolation technique.

One approach utilizing gas chromatography/infrared matrix-isolation spectrometry is disclosed in U.S. Pat. No. 4,158,772 issued to the present inventor and shown in schematic form in FIG. 1. In this approach, a vacuum chamber 11 contains a specular carousel 13 which may either have a plurality of sample surfaces (eight are shown in FIG. 1) or may be circular in cross section and provide a continuous sample surface. Also shown enclosed within the vacuum chamber are two concave mirrors 15, 17 aligned toward one of the sample surfaces of carousel 13. Two lenses or optical windows 19, 21 are installed within the vacuum chamber wall and aligned to admit and transmit light to and from the vacuum chamber 11. A beam of light, e.g., in the infrared (IR) spectrum, is provided by a light source and interferometer (or monochrometer) 23 and transmitted into the vacuum chamber through, for instance, mirrors 25, 29 and 27. Similarly arranged mirrors, for instance 31, 35 and 33, direct the return light beam once it has transitted the sample material into a detector within spectrometer 37 for analysis of the spectra of the sample material. The mirrors 15, 17 have spherical or elipsoidal surfaces for directing and focusing a light beam between the optical windows 19, 21 and the sample on a reflecting surface of carousel 13. Gas samples for analysis are provided from a source 39 such as a gas chromatography unit through inlet 38 to the sample block surfaces of carousel 13. A cryostat (not shown) cools the carousel 13 so as to freeze the gaseous sample material onto an appropriate sample block surface and a diffusion pump (not shown) is connected to the vacuum chamber 11 for maintaining a vacuum therein.

Although capable of providing accurate spectrographic data, this approach, as well as other prior art systems, suffers from various limitations which precluded their widespread acceptance and general use. One limitation involves the long effective focal length of the reflector configuration utilized in the system. This results in a more diffuse, larger image and reduced measurement sensitivity. In addition, the various reflectors in the system are all independently mounted thus making it substantially more difficult to accurately focus the incident light beam. For example, reflectors 15 and 17, which are positioned within the vacuum chamber 11, must not only be aligned with optical windows 19 and 21 mounted in a wall of the vacuum chamber, but also with mirrors 25, 27, 29, 31, 33 and 35. This number of reflectors arranged in a generally linear alignment makes precise beam positioning extremely difficult. Finally, the geometry of the optics requires the incident and reflected beams to circumscribe the vacuum chamber 11. In addition, the sample source 39 provides a gaseous sample to carousel 13 through the same vacuum chamber wall through which the incident and reflected beams are transmitted. The opposite side of the carousel 13 is nearly entirely enclosed by concave mirrors 15 and 17. Thus, visual access to the deposited sample for monitoring the aforementioned important conditions is a matrix-isolation system discussed above is virtually impossible in this system. The measurement accuracy of prior art gas chromatography/infrared matrix-isolation spectrometry systems, including that disclosed in the aforementioned patent, is therefore inherently limited by system configuration.

The gas chromatography/matrix-isolation apparatus of the present invention overcomes the aforementioned limitations of the prior art by providing a system in which the incident electromagnetic beam may be precisely positioned relative to the sample under investigation and the formation of the sample may be closely monitored to provide optimum sample deposition.

OBJECTS AND SUMMARY OF THE INVENTION

Accordingly, it is an object of the present invention to provide means for the improved spectroscopic analysis of a collected sample material.

It is another object of the present invention to provide an improved gas chromatography/matrix isolation device for the spectroscopic analysis of a collected gas sample.

Yet another object of the present invention is to provide for more accurate positioning of an electromagnetic beam with respect to a sample material irradiated in an absorption spectrometer measurement.

A further object of the present invention is to provide a gas chromatography/matrix-isolation device wherein the irradiation beam-directing optics system is disposed outside of the vacuum chamber in which the sample under analysis is deposited.

The present invention contemplates a gas chromatography/matrix-isolation device for the spectroscopic analysis of the absorption bands of a vacuum-deposited gas sample. A sample material is mixed with a carrier gas for transport into a vacuum chamber. The carrier gas is a mixture of helium ($>95\%$) and argon, krypton or nitrogen ($<5\%$). The sample is transported by the carrier gas and deposited on a rotating specular carousel having either a round surface or a plurality of deposition surfaces, e.g., hexagonal in shape, and located within the vacuum chamber. The helium gas is then pumped away with the sample material remaining in the deposited argon, krypton or nitrogen matrix for spectral analysis. A pair of parabolic mirrors direct an incident IR beam into the vacuum chamber and upon the sample and direct a reflected beam containing the absorption spectrum to a spectrometer for analysis. The two parabolic mirrors are located outside of the vacuum chamber and may be displaced together to provide more accurate incident beam positioning. In addition, beam index apertures are provided in the deposition surface (or surfaces) of the carousel to insure proper beam alignment with respect to the reflecting surfaces and a long focal length stereomicroscope is provided to permit monitoring of the sample deposition process. With the sample collector, as well as the sample delivery means, positioned outside of a zone bounded by the IR beam and with the IR examination area on the same side of the collector as the spectrometer, improved sample access and optical alignment is provided.

In another embodiment, gas chromatographically separated components of a sample are sequentially collected upon, or directly in front of, a plurality of cryogenically cooled infrared (IR) crystal detectors. An IR beam is then directed onto each of the IR crystal detectors to provide an IR spectrum of a separated component. An electrical signal derived from a detector is processed by a spectrometer to give an IR spectrum of the component in the matrix deposited on the detector surface or on an IR transparent film protecting the crystal. This approach thus makes use of cryogenically cooled IR detectors for improving the signal-to-noise ratio by several orders of magnitude while utilizing an optical system of substantially reduced complexity.

BRIEF DESCRIPTION OF THE DRAWINGS

The appended claims set forth those novel features believed characteristic of the invention. However, the invention itself, as well as further objects and advantages thereof, will best be understood by reference to the following detailed description of a preferred embodiment taken in conjunction with the accompanying drawings, where like reference characters identify like elements throughout the variuous figures, in which:

DESCRIPTION OF PREFERRED EMBODIMENT

Figure 2:
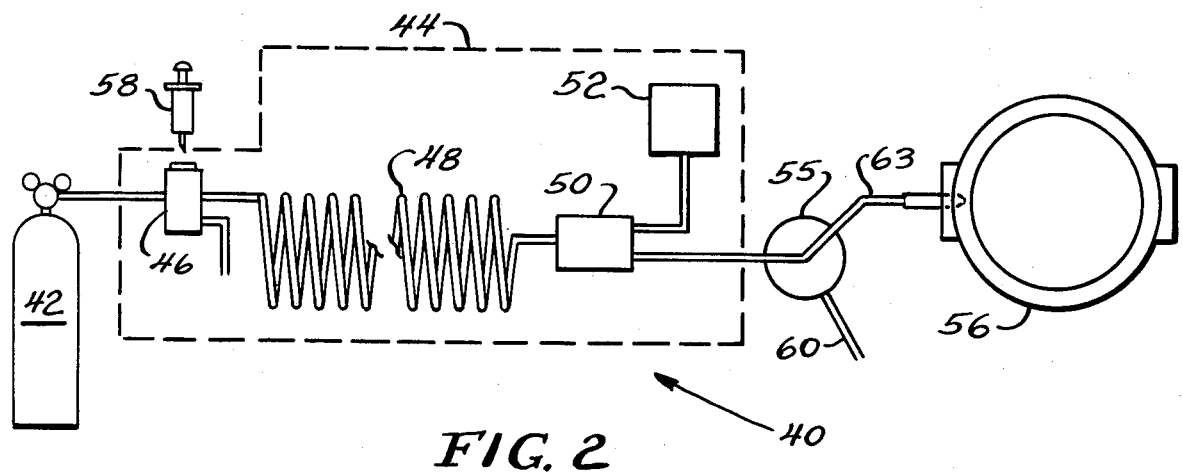
FIG. 2 is a simplified schematic of the gas flow of the carrier/matrix gas mixture for a gas chromatography/matrix-isolation system in accordance with the present invention.

Referring to FIG. 2, there is shown a simplified schematic illustration of the gas flow of the carrier/matrix gas mixture for a gas chromatography/matrix-isolation system 40 in accordance with the present invention.

The gas chromatography/matrix-isolation system 40 includes a gas chromatograph 44 coupled to a source of a mixture of carrier and matrix gases 42. The gas mixture source 42 provides a mixture of a carrier gas, such as helium or hydrogen, and a matrix gas such as argon, krypton or nitrogen. In a preferred embodiment, the premixed supply of inert gas containing preferably argon in an abundance of 1 to 5 volume per cent in helium is delivered to a conventional capillary column 48 via an injection port 46. The capillary column 48 is included in a gas chromatograph 44, such as a Perkin-Elmer Model 5800 gas chromatograph. A flow of approximately 1 cm$^3$/mm of the gas mixture carries the compound through the capillary column 48 where the separation of compounds occurs. At the exit of the capillary column 48, between the capillary column and a flame ionization detector 52 of the gas chromatograph 44, a flow splitting junction 50 is provided which diverts approximately ⅔ of the effluent gas stream from infrared analysis. This remaining ⅓ of the gas stream goes to the gas chromatographic flame ionization detector 52 for use in generating a gas chromatogram in the usual manner.

The sample material is typically a liquid solution containing a plurality of dissolved compounds and is injected into the gas stream through a septum by use of a hypodermic syringe 58. The sample vaporizes rapidly into the carrier/matrix gas mixture which is typically held at an elevated temperature (100° to 300° C.). The carrier gas transports the sample material through the chromatographic column 48 where separation of the compounds occurs due to differing retention times for different compounds according to the well established principles of gas chromatography. The matrix gas is used to collect and confine the sample material in matrices of the condensed inert matrix gas within cryogenic sample collector 56 for spectrographic analysis. The carrier gas is noncondensable and preferably of low molecular weight and is pumped from the cryogenic sample collector 56 by means of a vacuum pump (not shown). The matrix-forming condensable gas has a higher molecular weight than the carrier gas and is used in low concentrations (approximately 1–5%). The 3-way capillary valve 55 in the line between the flow splitting junction 50 and the cryogenic sample collector 56 allows the option of directing the effluent either to a dump line 60 during initial testing of the gas chromatography/matrix-isolation system 40 or to the cryogenic sample collector 56 where the desired sample collection and infrared spectral examinations take place.

The cryogenic sample collector 56 includes a cold reflecting surface (not shown in FIG. 2) which typically is rotated to present either a large number of collection sites or a single collection surface or area to a heated delivery line 63 from the gas chromatograph 44. The gas chromatograph 44 is preferably of the wall-coated open tubular capillary column type which permits a lower carrier gas flow to be utilized. Sample material separation is accomplished within gas chromatograph 44 using a 0.3 mm inner diameter (ID) fused silica bonded phase capillary column.

Using a low molecular weight noncondensable carrier gas together with a low concentration of matrix-forming condensable gas of higher molecular weight, results in each component eluted from the gas chromatograph 44 being typically collected in a matrix area less than 1 mm$^2$. By contrast, the use of a pure condensable inert gas, such as argon or nitrogen, as the gas chromatographic carrier followed by collection of the carrier and separated components at low temperature yields poor results. This is due to the high rate of gas delivery required by the gas chromatograph 44 which does not permit collection of the carrier and separated components in a small area. In addition, the concentration of sample in a condensed gas in the aforementioned approach is too low to yield adequate infrared absorption.

Figure 3:
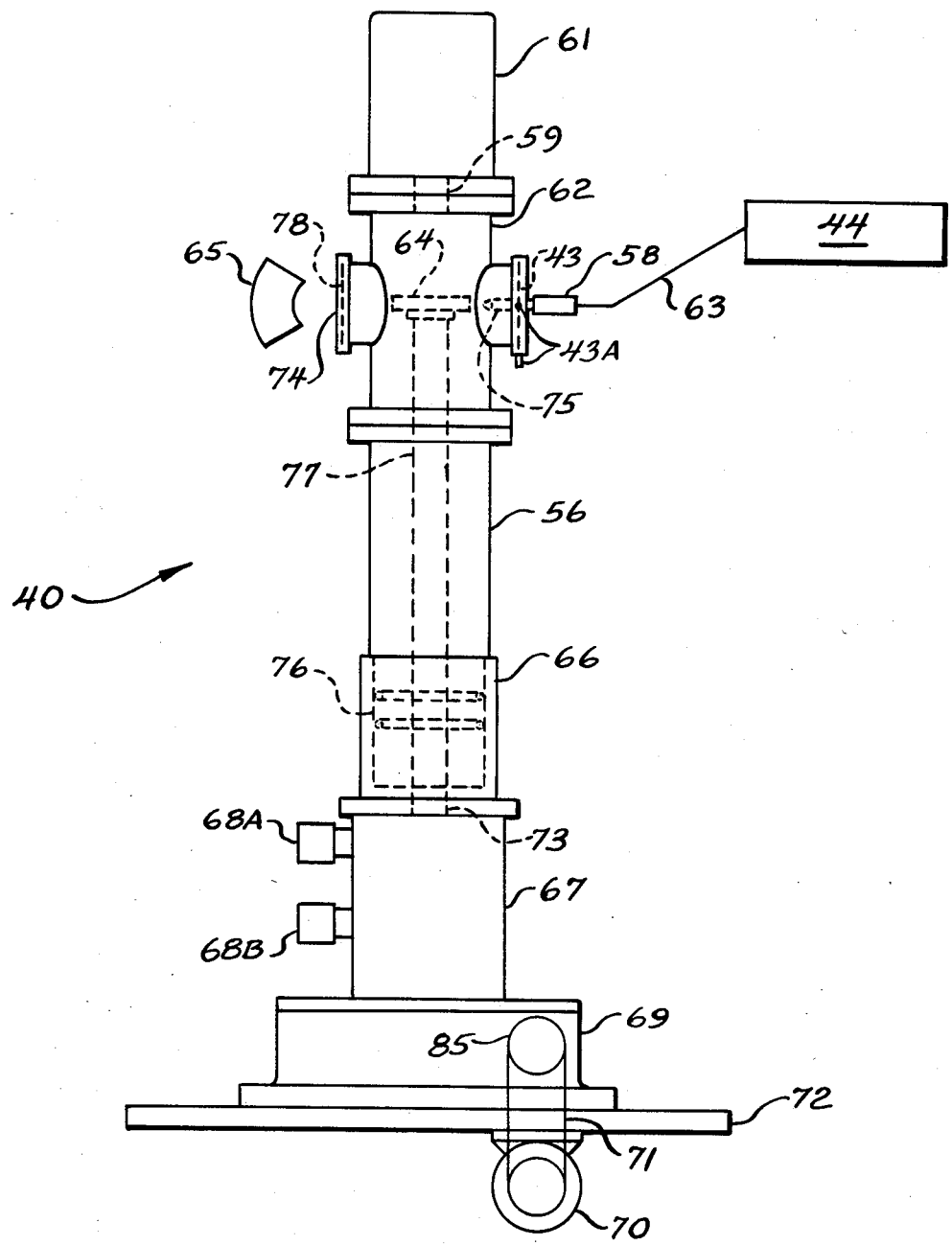
FIG. 3 is a partially cutaway side view of a gas chromatography/matrix-isolation apparatus in accordance with the present invention.

Referring to FIG. 3, there is shown a partially cutaway side view of a gas chromatograph/matrix-isolation apparatus 40 in accordance with the present invention. The gas chromatography/matrix-isolation system 40 includes an evacuated cryogenic sample collector 56, a spectrometer (not shown in FIG. 3), a beam-condensing optical system primarily comprised of a pair of paraboloid mirrors 65 for projecting an IR beam through the sample and back to the spectrometer, and a gas chromatograph 44. The sample material is provided to the cryogenic sample collector 56 from a sample source, such as the aforementioned gas chromatograph 44, via the combination of a heated delivery line 63 and a nozzle 58. The cryogenic sample collector 56 is coupled at an upper portion thereof to a vacuum pump 61 and at a lower portion thereof to a cryostat 67. The cryostat 67 is used for freezing the gaseous sample material introduced into the cryogenic sample collector 56 onto an appropriate sample block surface such as a specular carousel 64 positioned therein. Cryostat 67 is connected to a low temperature source (not shown) via refrigerant connectors 68A, 68B. Vacuum pump 61 maintains a vacuum within the cryogenic sample collector 56 and pumps away the carrier gas. In a preferred embodiment, vacuum pump 61 is a Balzers Model 300 turbomolecular pump having a pumping speed for helium of approximately 200 L/sec. Vacuum pump 61 maintains the chamber pressure at approximately $3 \times 10^{-6}$ torr, while the rate of flow of matrix/carrier gas into the cryogenic sample collector 56 is approximately 1 cm$^3$/min. The specular carousel 64 is connected to a cryostat duct/support shaft 77 which serves to maintain the specular carousel in proper position within the cryogenic sample collector 56 and at a low temperature permitting the sample/matrix material to condense thereupon. The specular carousel 64 is comprised of a highly reflective lateral surface, or surfaces, and rotates at approximately 1 revolution per hour resulting in the formation of a band of collected material partially or entirely around its circular circumference. The deposit line of the sample material and the pair of paraboloid mirrors 65 may be raised and lowered as described below to obtain and analyze new bands of collected material. This permits more than one sample material to be condensed upon the specular carousel 64 for spectrographic analysis.

The cryogenic sample collector 56 itself has four ports:
(1) A high vacuum port 59;
(2) A cryostat feedthrough port 73;
(3) An infrared port 74 containing a potassium chloride window 78 approximately 1.5 mm thick and 8 mm in diameter, with the window mounted so as to be approximately 2.5mm from the lateral surface of the specular carousel 64 while facing the pair of paraboloid mirrors 65; and
(4) A nozzle/inspection port 58 which includes a pyrex window 43 approximately 5 mm thick and 40 mm in diameter.

A central hole in the pyrex window 43 accommodates a ⅜ in. outer diameter (OD) by 0.010 in. wall stainless steel tube 75 which serves as a stand off and feedthrough for a heated copper block that houses a capillary tube carrying the carrier/matrix gas from the heated delivery line 63. The pyrex window 43 is positioned on an o-ring seal which is mounted in a frame that allows the window and nozzle to be moved horizontally or vertically by one set of three radially oriented screws 43A coplanar with the window or to be moved closer or farther away from the specular carousel 64 by three jack screws translating the frame and plane of the pyrex window 43.

The cryostat feedthrough port 73 is connected to the cryogenic sample collector 56 via an extension to a rotatable o-ring sealed joint 66. An upper portion of the cryostat feedthrough port 73 is connected to an expander module 76 of a closed cycle helium refrigerator (not shown). A cryostat duct/support shaft 77 in the form of a piston housing extends from the expander module 76 into the cryogenic sample collector 56 for supporting and cooling the specular carousel 64. Motion is imparted to the expander module 76 and thence to the specular carousel 64 by means of a machinist's rotary indexing table 69. The drive shaft 85 to the rotary table 69 is driven via a drive belt 71 by a computer-controlled stepping drive motor 70. The drive motor 70 and control system in a preferred embodiment consist of a Compumotor Model 83 motor and a Model 2100 indexer connected through an RS-232 interface line to the computer (not shown) of the spectrometer.

Although a gas chromatograph 44 is used to separate gaseous components into distinct portions or bands that are sequentially discharged for analysis in the present invention, this invention is not limited to this type of gas sample source. For example, gas samples may also be provided from other sources such as the decomposition or volatilization of sample material over a temperature range or as separate unrelated samples.

Figure 4:
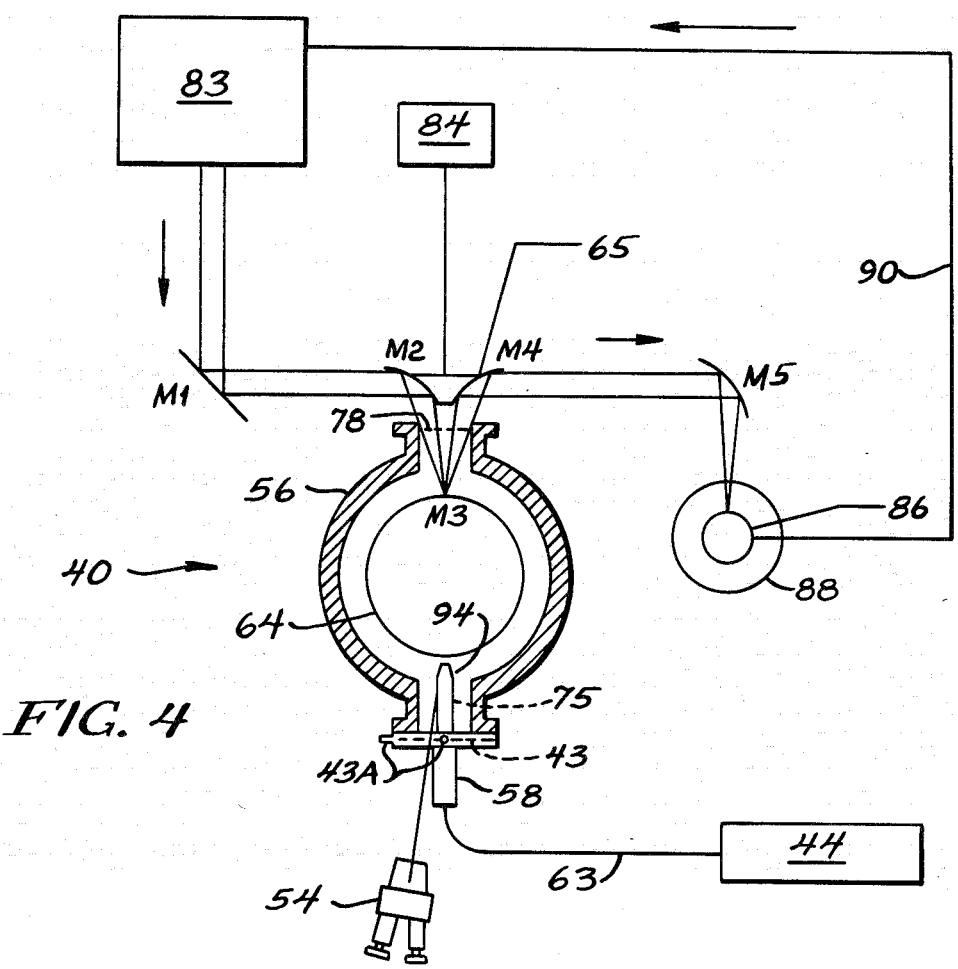
FIG. 4 is a top sectional view of the gas chromatography/matrix-isolation apparatus of FIG. 3 illustrating in particular the path of the collimated incident and reflected beams.

Referring to FIG. 4, there is shown a top sectional view of the gas chromatography/matrix-isolation system 40 of FIG. 3. The path of a collimated beam of infrared light is shown in FIG. 4 emerging from an IR spectrometer 83, which in a preferred embodiment is a Nicolet Model 6000 Fourier transform infrared spectrometer, and is reflected from plane mirror M1. The infrared beam is then directed to a pair of paraboloid mirrors 65 shown in FIG. 4 as M2 and M4. Paraboloid mirrors M2, M4 are respective segments cut from an electroformed parabolic reflector. Each of paraboloid mirror sections M2, M4 are nominally 120° off-axis with respect to the master paraboloid from which it was cut. The focii of mirrors M2 and M4 are at the point of sample inspection on a lateral surface of specular carousel 64. This lateral surface of specular carousel 64 forms yet another reflective surface, or mirror, M3. At M3 the infrared beam passes through the matrix of solid argon in which molecules of the sample material are trapped and is reflected from the mirror surface M3 of the specular carousel 64. The IR beam is reflected from mirror surface M3 onto a second paraboloid mirror M4 which is a parabolic reflector identical to M2 but inverted. Mirror M4 intercepts the infrared beam reflected from M3 and emerging from the argon matrix and collimates the beam in directing it toward mirror M5. Mirrors M2 and M4 are precisely prealigned so that their focii are exactly coincident. If mirrors M2 and M4 are removed from the path of the infrared beam, the beam passes directly to mirror M5. The pair of paraboloid mirrors 65 which includes mirrors M2 and M4 are attached to displacement means 84 which may include a set of three translation stages so that mirrors M2, M4 can be moved in any of three mutually perpendicular directions allowing their focus to be properly positioned with respect to specular carousel 64. Mirror M5 is a parabolic reflector which focuses the beam from mirror M4 onto a mercury cadmium telluride infrared detector element 86 located within a liquid nitrogen cooled dewar 88. A signal from the infrared detector 86 is output therefrom and provided to the IR spectrometer 83 via line 90 to permit an infrared spectrum to be produced.

Also shown in FIG. 4 is a 10× power stereomicroscope 54 with a working distance of approximately 9 inches. Stereomicroscope 54 is used to set the position of the 0.006 in. (0.15 mm) inner diameter (ID) capillary tip 94 with respect to the specular carousel 64. A small flat mirror (not shown) within the cryogenic sample collector 56 and positioned above the specular carousel 64 provides a view of the 0.006 in. (0.15 mm) gap between the capillary tip 94 and the surface of the specular carousel 64. Referring to FIG. 3, the use of flexible hoses (not shown) coupled to refrigerant connectors 68A, 68B between the cryostat expander module 76 and the remotely located compressor module (not shown) allows the cryostat expander module to be rotated 1½ turns for the collection and display of samples on the specular carousel 64. The gas samples of the material to be analyzed are provided from the gas chromatograph 44 via a capillary line passing through the combination of heated delivery line 63 and the nozzle/inspection port 58 through the copper tube 75 and thence discharging into the cryogenic sample collector 56.

From FIGS. 3 and 4, it can be seen that the incident and reflected IR beams enter and exit the cryogenic sample collector 56 via a single optical window 78. In addition, it can be seen that the path of the IR beam and the location of the inlet through which the sample material is deposited upon the specular carousel 64 are on opposite sides of the specular carousel and the cryogenic sample collector 56.

Stereomicroscope 54 permits the size and thickness of the sample/matrix material mixture deposited upon the specular carousel 64 to be closely monitored and controlled. The monitoring of these parameters is important because in order to optimize IR sensitivity, the sample must be condensed in as small an area as possible. In addition, the amount of gas deposited in any one spot is limited. As the thickness of a deposit approaches approximately 0.5 mm, the deposited material has sufficient insulating capacity to impede the condensation of additional gas. In addition, sample flaking from the cold surface of the specular carousel 64 becomes probable as the thickness increases. The ability to optically view the sample to be analyzed as it is deposited upon the specular carousel 64 substantially increases the accuracy and reproducibility of the spectrographic analysis of the sample. In addition, conventional means such as the aforementioned three radially oriented screws 43A may be provided to displace the capillary tip along three mutually perpendicular axes in order to permit a more close inspection of the deposited sample material by means of stereomicroscope 54 upon the lateral surface of specular carousel 64.

Figure 5:
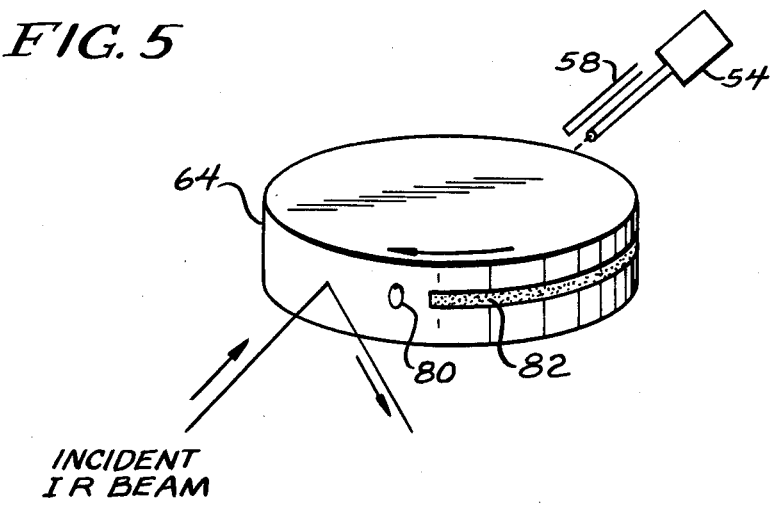
FIG. 5 shows a perspective view of a specular carousel for use in the gas chromatography/matrix-isolation apparatus of the present invention.

Referring to FIG. 5, there is shown a perspective view of a specular carousel 64 provided with an alignment aperture 80 also in accordance with the present invention. An incident IR beam is directed on a lateral surface of the specular carousel 64 which rotates in the direction of the arrow shown in the figure. A band of matrix material 82 within which is positioned the sample being analyzed is deposited upon the lateral surface of the specular carousel 64 by means of a nozzle 58. Nozzle 58 is positioned in close proximity to the lateral surface of specular carousel 64 and is coupled to the heated delivery line 63 for directing the sample material/matrix gas onto the lateral surface of the specular carousel 64. The incident IR beam is reflected by the lateral surface of the specular carousel 64 and is provided to suitable spectrometric detectors for analyzing the spectrographic characteristics of the sample material deposited within the matrix 82. A stereomicroscope 54 is positioned adjacent nozzle 58 to permit visual monitoring of the deposition of the sample material upon the specular carousel 64. Located within the lateral surface of specular carousel 64 immediately adjacent the band matrix 82 is an alignment aperture 80. When specular carousel 64 rotates to the position where the IR beam is incident upon the alignment aperture 80, the IR beam is no longer reflected by the specular carousel and the absence of the reflected beam is detected by the spectrometer. With the angular velocity of the specular carousel 64 known, the position of the incident IR beam with respect to the band matrix 82 may be precisely determined for highly accurate spectrographic readings. If several band matrices 82 are deposited upon the lateral surface of specular carousel 64 as it is displaced along its axis of rotation, the lateral surface of specular carousel 64 may be provided with a plurality of alignment apertures 80 each associated with a respective band matrix to insure proper positioning of the incident IR beam with respect to each of the band matrices.

Figure 6:
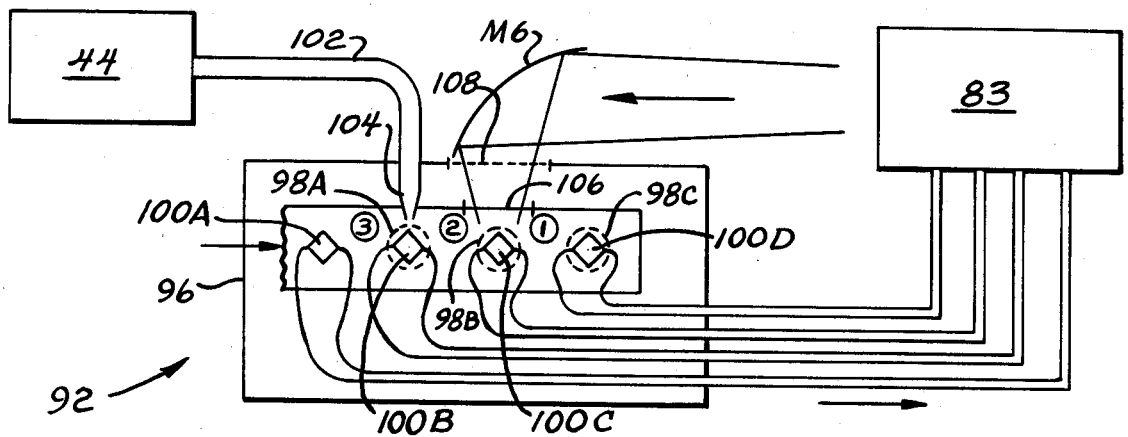
FIG. 6 is a simplified schematic diagram of another embodiment of a gas chromatography/matrix isolation apparatus in accordance with the present invention.

Referring to FIG. 6, there is shown a simplified schematic diagram of yet another embodiment of a gas chromatography/matrix isolation system 40 in accordance with the present invention. The system of FIG. 6 includes a vacuum chamber 96 coupled to a gas chromatograph 44 which provides gas samples for analysis thereto via delivery tube 102. Positioned within vacuum chamber 96 are a plurality of cryogenically cooled infrared detectors 100A, 100B, 100C, and 100D mounted to a linearly displaceable cryogenic cold stage 106. The gas chromatographically separated components are collected upon or directly in front of each of the cryogenically cooled infrared detectors as they are linearly displaced in the direction of the arrow shown in the figure in front of the nozzle 104 at the end of delivery tube 102. An IR spectrometer 83 provides a collimated beam of light via mirror M6 and optical window 108 into the vacuum chamber 96 and upon each of the IR detectors as they pass adjacent to optical window 108. Samples of the material to be analyzed are deposited upon each of the IR detectors as each passes, in turn, in front of nozzle 104. Therefore, sample matrices 98A, 98B and 98C are respectively deposited upon IR detectors 100B, 100C and 100D.

Figure 7:
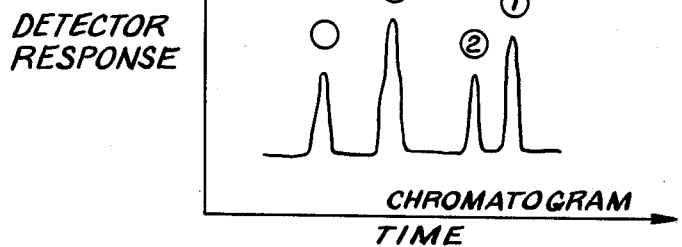
FIG. 7 illustrates the sequential deposition in the gas chromatography/matrix isolation apparatus of FIG. 6 of various samples upon several low noise, low temperature photoconductive or other type of infrared-responsive detector crystals in accordance with the present invention.
Figure 8A:
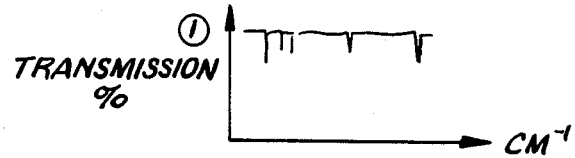
FIGS. 8A, 8B and 8C illustrate typical IR spectra for various samples analyzed in the gas chromatography/matrix isolation apparatus of FIG. 6.
Figure 8B:
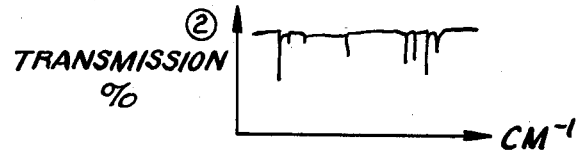
Figure 8C:
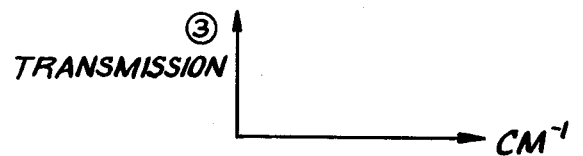

As in the case of the earlier embodiments, the effluent from the gas chromatograph 44 is mixed with a condensible inert gas in the appropriate ratio to give matrix-isolated sample molecules when the mixture is condensed. The separated components in the gas stream are directed sequentially onto low-noise, low-temperature photoconductive or other type of infrared-responsive detector crystals 100A, 100B, 100C and 100D, which are in thermal contact with a cryostatic surface 106 at a sufficiently low temperature to allow condensation of the mixture onto the crystal (or onto an infrared-transparent film protecting the crystal). The IR detectors may, for example, be comprised of HgCdTe crystals. Each of the IR detectors 100A, 100B, 100C and 100D are electrically coupled to the IR spectrometer 83. The electrical signal obtained through the operation of a given detector is used by the IR spectrometer to provide an infrared spectrum of the component and the matrix on the detector surface. A sample gas chromatogram is shown in FIG. 7 where the numbers 1, 2 and 3 represent, respectively, IR detectors 100D, 100C, 100B. FIGS. 8A, 8B and 8C similarly show representative IR spectra derived from the aforementioned IR detectors.

Figure 1:
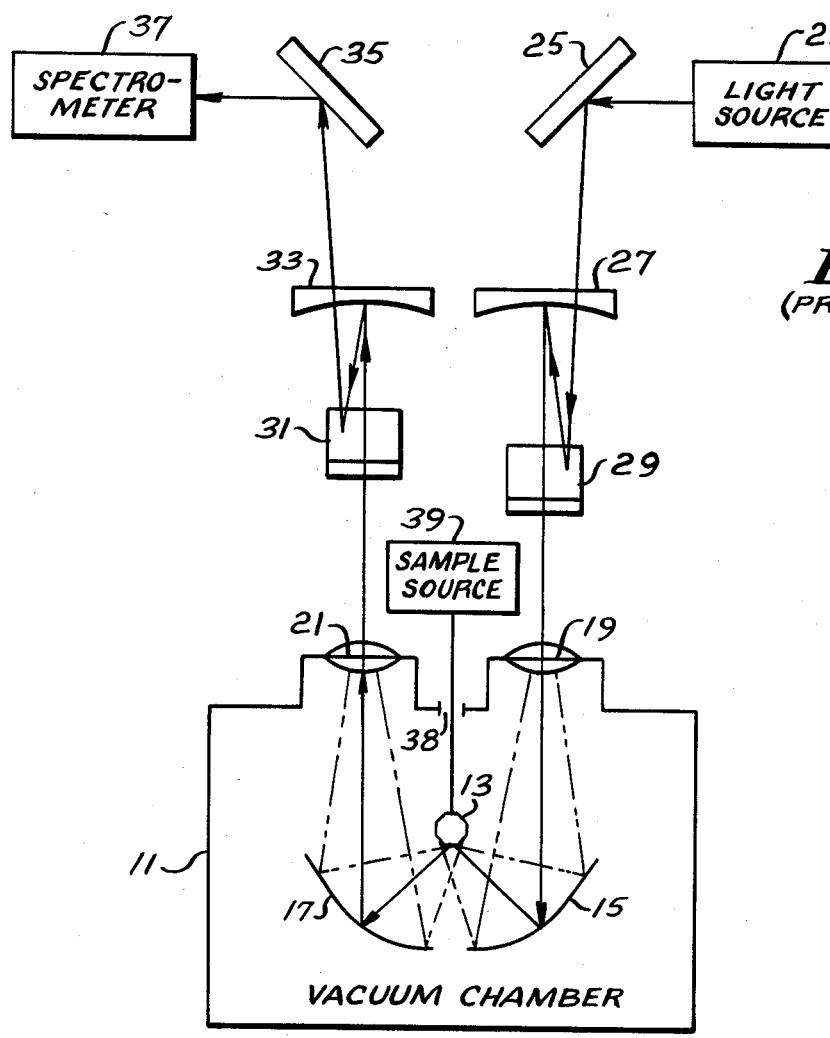
FIG. 1 is a schematic illustration of the optical path of a prior art device for spectrometric examination of matrix-isolated samples.

There are several advantages to the arrangement of FIG. 6. First, it makes use of cryogenically cooled infrared detectors which provide an improvement of several orders of magnitude in signal-to-noise ratio when compared to room temperature infrared detectors of the type used in previous gas chromatograph/matrix isolation systems. The system shown in FIGS. 3 and 4 also uses a cooled detector, but it is housed in a separate dewar. A liquid nitrogen cooled external detector could have been used for the system of FIG. 1. Secondly, this embodiment of the present invention incorporates the detector immediately aft of the sample so that the complexity of the optical system is substantially reduced and does not require highly precise alignment of the infrared beam with respect to the sample and detector. In addition, unwanted motion of the sample under analysis with respect to the IR detector is eliminated.

There has thus been shown an improved gas chromatography/matrix-isolation apparatus for the matrix isolation of individual gas bands from a gas chromatographic separation and for the spectroscopic analysis of the individual gas bands. A pair of off-axis parabolic mirrors are positioned outside of a vacuum chamber in which the gas-sample is deposited upon a specular carousel for directing an incident IR beam upon the sample through an optical window in the vacuum chamber. The pair of parabolic mirrors may be displaced together for more easily and accurately focusing and positioning the incident IR beam. A sample feed inlet is positioned in the vacuum chamber on a lateral portion thereof opposite to that of the spectrometer/reflector combination for improved sample access. Sample access is further improved by the positioning of the sample collector outside of a zone bounded by the incident and reflected IR beams. By thus improving sample access, the deposition of the sample/matrix mixture may be closely monitored for highly accurate spectrographic analysis. In addition, the rotating specular carousel is provided with a plurality of apertures adjacent respective band matrices deposited thereon to facilitate accurate positioning of the incident IR beam relative to the gas-samples being analyzed. In another embodiment, chromatographically separated, matrix-isolated sample molecules are deposited directly upon cryogenically cooled low-noise, low-temperature photoconductive IR-responsive crystals. An electrical signal from an IR-irradiated detector is provided to an IR spectrometer for analysis.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. Apparatus for the collection and spectroscopic analysis of a sample in a matrix, said apparatus comprising:
   an evacuated chamber having an optical window in a first wall portion thereof;
   a cryogenically cooled specular sample carrier rotatably supported along its longitudinal axis within said evacuated chamber and including an external, reflecting lateral surface;
   inlet means positioned in a second wall portion of said evacuated chamber adjacent to said specular sample carrier for depositing a sample material intermixed with matrix material onto the lateral reflecting surface of said sample carrier whereupon the mixture of said sample material and said matrix material solidifies on said cooled specular sample carrier, wherein said first and second wall portions form facing sections of said evacuated chamber;

illumination means for generating a beam of electromagnetic radiation;

detection means positioned outside of said evacuated chamber and optically communicating with and responsive to a modulated beam of electromagnetic radiation incident thereon for measuring the spectral characteristics thereof;

first and second coupled parabolic reflecting means having a common focal point and positioned outside of said evacuated chamber for respectively directing said beam of electromagnetic radiation through said optical window and onto the mixture of said sample and matrix materials and for directing the beam of electromagnetic radiation reflected from said lateral reflecting surface through said optical window to said detection means wherein the spectral characteristics of said beam are measured and said sample is analyzed;

alignment means including an aperture located on the lateral reflecting surface of said sample carrier for proper positioning of said beam of electromagnetic radiation relative to the sample and matrix material mixture deposited thereon, whereby no input is provided to said detection means when said beam of electromagnetic radiation is incident upon said aperture; and displacement means coupled to the combination of said first and second parabolic reflecting means for adjusting the position and the focal point of said beam of electromagnetic radiation relative to said alignment means on said specular sample carrier for improved spectroscopic analysis of said sample.

2. The apparatus of claim 1 further including third and fourth reflecting means respectively aligned with said first and second parabolic reflecting means for directing said incident beam of electromagnetic radiation onto said first parabolic reflecting means from said illumination means and for directing said reflected beam of electromagnetic radiation from said second parabolic reflecting means to said detection means.

3. The apparatus of claim 1 further including optical viewing means coupled to said vacuum chamber for observing the deposition of said sample and matrix material mixture upon the lateral reflecting surface of said sample carrier.

4. The apparatus of claim 3 wherein said optical viewing means includes a stereomicroscope having a long focal length, with said stereomicroscope focussed at the point on the lateral reflecting surface of said sample carrier where said sample and matrix material mixture is deposited from said inlet means.

5. The apparatus of claim 3 further including control means coupled to said inlet means and to said optical viewing means for effecting the coincidence of the deposition location of said sample and matrix material and the viewing area of said optical viewing means on the lateral surface of said sample carrier.

6. The apparatus of claim 1 further including a gas chromatograph coupled to said inlet means, said gas chromatograph containing said sample material for mixing with said matrix material therein for delivery to said evacuated chamber.

7. The apparatus of claim 6 further including means defining and containing a source of carrier/matrix gas mixture coupled to said gas chromatograph for removing said sample material therefrom and mixing said sample material with said matrix gas for deposition on said specular sample carrier.

8. The apparatus of claim 7 wherein said means for defining a source of carrier/matrix gas mixture includes means defining and containing a supply of hydrogen or helium carrier gas.

9. The apparatus of claim 7 wherein said means for defining a source of carrier/matrix gas mixture includes means defining and containing a supply of argon, krypton or nitrogen matrix gas.

10. The apparatus of claim 7 further including evacuation means coupled to said chamber for the evacuation thereof and the removal of said carrier gas from said chamber.

11. The apparatus of claim 7 wherein said means for defining a source of carrier/matrix gas mixture includes means defining and containing a supply of less than 5% of matrix gas and greater than 95% of carrier gas.

12. The apparatus of claim 1 further including cryogenic means coupled to said specular sample carrier for supporting and reducing the temperature of said specular sample carrier within said evacuated chamber.

13. The apparatus of claim 12 further including rotatable support means for supporting and rotating said cryogenic means and said specular sample carrier during the deposition of said carrier/matrix gas mixture thereon.

14. The apparatus of claim 13 further including stepping motor means coupled to said rotatable support means for rotating said specular sample carrier.

15. The apparatus of claim 13 further including an expander module coupling said cryogenic means to said specular sample carrier.

16. Apparatus for the collection and spectroscopic analysis of a sample material in a matrix, said apparatus comprising:

means defining an enclosed evacuated chamber;

inlet means in said means defining said evacuated chamber for introducing said sample material in the form of a gas therein;

an optical window in a wall of said means defining said evacuated chamber for directing a beam of electromagnetic radiation into said chamber;

a plurality of separate infrared detector crystals positioned in said means defining said evacuated chamber for receiving said sample material in the form of a matrix deposited thereon;

cryostatic cooling means coupled to each of said infrared detector crystals;

displacement means for sequentially displacing each of said infrared detector crystals immediately adjacent to said inlet means and in alignment with said optical window wherein said sample material is deposited in turn upon each of said infrared detector crystals as each detector crystal is positioned immediately adjacent to said inlet means;

focusing means for concentrating a beam of electromagnetic radiation incident thereon; and spectrometric means coupled to each of said infrared detector crystals for directing a beam of electromagnetic radiation via said focusing means and said optical window into said means defining said evacuated chamber and through said deposited sample material onto each of said infrared detector crystals as each of said infrared detector crystals is positioned in alignment with said optical window by said displacement means for examining the spectral characteristics of said sample material.

17. Apparatus as in claim 16 wherein said detector crystals include infrared responsive HgCdTe crystals.

* * * * *